US008063005B2

(12) United States Patent
Kalidindi

(10) Patent No.: US 8,063,005 B2
(45) Date of Patent: Nov. 22, 2011

(54) PERSONAL CARE FORMULATIONS WITH SIMULTANEOUS EXFOLIANT, CLEANSING AND MOISTURIZING PROPERTIES

(76) Inventor: Sanyasi Raju Kalidindi, East Brunswick, NJ (US)

( * ) Notice: Subject to any disclaimer, the term of this patent is extended or adjusted under 35 U.S.C. 154(b) by 382 days.

(21) Appl. No.: 12/331,197

(22) Filed: Dec. 9, 2008

(65) Prior Publication Data
US 2009/0149362 A1 Jun. 11, 2009

Related U.S. Application Data

(60) Provisional application No. 61/012,624, filed on Dec. 10, 2007.

(51) Int. Cl.
C11D 3/12 (2006.01)
A61K 9/50 (2006.01)

(52) U.S. Cl. ........ 510/139; 510/119; 510/130; 510/136; 510/158; 510/159; 510/405; 510/407; 424/499; 424/757; 424/750; 424/488

(58) Field of Classification Search ............... 510/119, 510/121, 130, 136, 137, 138, 139, 158, 159, 510/405, 407; 424/401, 499, 725, 488, 484, 424/757, 750
See application file for complete search history.

(56) References Cited

U.S. PATENT DOCUMENTS

| | | | | |
|---|---|---|---|---|
| 4,238,509 A | * | 12/1980 | Evans et al. | 514/777 |
| 4,673,526 A | * | 6/1987 | Zabotto et al. | 510/139 |
| 5,589,195 A | * | 12/1996 | Potter | 424/499 |
| 5,620,692 A | | 4/1997 | Potter et al. | |
| 5,622,690 A | * | 4/1997 | Potter et al. | 424/59 |
| 5,720,961 A | * | 2/1998 | Fowler et al. | 424/401 |
| 5,801,134 A | * | 9/1998 | Righton | 510/130 |
| 5,817,608 A | | 10/1998 | Bell | |
| 5,871,756 A | | 2/1999 | Jeffcoat et al. | |
| 5,879,684 A | * | 3/1999 | Fox | 424/401 |
| 6,248,338 B1 | * | 6/2001 | Muller et al. | 424/401 |
| 6,277,362 B1 | | 8/2001 | Ita | |

(Continued)

FOREIGN PATENT DOCUMENTS
EP 1106173 6/2001
(Continued)

OTHER PUBLICATIONS

USDA National Nutrient Database "Oats" pdf http://www.nal.usda.gov/fnic/foodcomp/cgi-bin/list_nut_edit.pl.*

(Continued)

*Primary Examiner* — Mark Eashoo
*Assistant Examiner* — Jane L Stanley
(74) *Attorney, Agent, or Firm* — Amin Talati, LLC; Janine A. Moderson

(57) ABSTRACT

A non-aqueous cleansing formulation having cleansing, moisturizing and/or exfoliating properties includes an oil phase and a natural surfactant derived from legumes and/or grains. The oil phase can include an oil component and a thickening agent. The natural surfactant can be in the form of a particulate flour product derived from *Vigna radiata, Vigna mungo, Glycine max, Cicer aerientinum, Vigna unguicalata, Pisum sativum, Phaseolus vulgaris*, or combinations thereof, which is dispersed in the oil phase. The flour product suitably includes a high protein flour to emulsify the oil phase and provide improved cleansing action. Such non-aqueous cleansing formulation can be used as skin care products, hand cleansers, hair cleaners or general use cleansers. Advantageously, the cleansing formulations are free of synthetic soaps and/or synthetic surfactants.

19 Claims, 2 Drawing Sheets

U.S. PATENT DOCUMENTS

| | | |
|---|---|---|
| 6,294,179 B1 * | 9/2001 | Lee et al. ............... 424/401 |
| 6,368,579 B1 | 4/2002 | Barr |
| 6,387,382 B1 | 5/2002 | Saleh et al. |
| 6,416,788 B1 | 7/2002 | Barr |
| 6,464,991 B1 | 10/2002 | Walele et al. |
| 6,506,375 B1 | 1/2003 | Barr |
| 6,531,422 B1 * | 3/2003 | Casariego et al. ........ 501/71 |
| 6,753,020 B1 | 6/2004 | Mayne |
| 6,924,256 B2 * | 8/2005 | Massaro et al. .......... 510/119 |
| 7,297,668 B2 * | 11/2007 | Johansson et al. ....... 510/157 |
| 2002/0028225 A1 * | 3/2002 | Lee et al. ............... 424/401 |
| 2002/0058076 A1 | 5/2002 | Paufique |
| 2003/0133900 A1 * | 7/2003 | McLaughlin ........... 424/70.22 |
| 2004/0161435 A1 * | 8/2004 | Gupta .................... 424/401 |
| 2004/0198620 A1 * | 10/2004 | Johansson et al. ....... 510/130 |
| 2005/0281851 A1 * | 12/2005 | Cap ....................... 424/401 |
| 2006/0246030 A1 | 11/2006 | Paufique |
| 2006/0257333 A1 | 11/2006 | Kauranen |
| 2007/0224136 A1 | 9/2007 | Dasgupta et al. |
| 2008/0292651 A1 * | 11/2008 | Zimmerman et al. ... 424/195.17 |
| 2009/0169652 A1 * | 7/2009 | Osborne ................. 424/727 |

FOREIGN PATENT DOCUMENTS

| | | |
|---|---|---|
| WO | 99/02267 | 1/1999 |
| WO | 99/52500 | 10/1999 |
| WO | 2004/071483 | 8/2004 |

OTHER PUBLICATIONS

USDA National Nutrient Database "Soybeans, mature seeds, raw" pdf http://www.nal.usda.gov/fnic/foodcomp/cgi-bin/list_nut_edit.pl.*

* cited by examiner

PERSONAL CARE FORMULATIONS WITH SIMULTANEOUS EXFOLIANT, CLEANSING AND MOISTURIZING PROPERTIES

This application claims the benefit of earlier filed U.S. Patent Application Ser. No. 61/012,624 filed on 10 Dec. 2007.

FIELD OF THE INVENTION

The present invention relates to a personal care formulation having exfoliant, cleansing and moisturizing properties, and, more particularly, a natural, non-aqueous personal care formulation which includes high protein legume or grain flour dispersed in an oil phase.

BACKGROUND

Synthetic as well as natural agents have been used for cleansing purposes. Soaps, surfactants and synthetic detergents have been used for decades for skin and hair cleansing. The objective of cleansing is to remove surface dirt, makeup, the top layer of dead skin cells and potentially harmful microorganisms.

Soaps are made by reacting oils with alkali and are very efficient in removing dirt by emulsification. Unfortunately, there are two problems with soaps: drying; and irritation of the skin due to excessive cleansing action and increased pH of the skin. Surfactants are typically synthetic compounds or materials which are good emulsifiers, but may be harsh to the skin. Synthetic detergents generally offer a better choice because their pH may be adjusted to that of skin, but again they may dry the skin too much and cause irritation. Both soap and the surfactants may be irritating to the eyes and may cause allergic reactions in some people. In addition formulations containing soap or surfactants typically provide little or no exfoliating or moisturizing effect, thus requiring the use of a separate exfoliant formulation and a moisturizing lotion or cream.

Natural agents used for cleansing include, for example, Shikakai (*Acacia concinna*), Soapwort (*Saponaria officinalis*) and/or Ritha (*Sapindus mukorossi*). These plant products have powerful saponins and are good cleansers, but they suffer from the same disadvantages of soap and synthetic surfactants, namely, skin and eye irritation. They may also be poisonous. For example, when ingested in excess, Soapwort destroys red blood cells and causes paralysis of the vasomotor center.

Another traditional method of cleansing, without the use of soap or a synthetic surfactant, involves rubbing the body with a vegetable oil, such as, for example, sesame oil, coconut oil or the like, followed by rubbing with a paste made from a grain flour. Such grain flours may, for example, be derived from Black Gram (*Vigna mungo*), Green Gram (*Vigna radiata*), Soy (*Glycine max*), Basan and/or Chickpea (*Cicer aerientinum*) and are typically or commonly combined with water and/or milk to form the paste. However, this method suffers from many disadvantages: (1) the paste of flour with water is susceptible to microbial growth and is physically unstable, requiring preparation of the paste just before use; (2) by making an aqueous paste of the grain flour, the exfoliant properties will be lost because the grain flour loses its grain structure and strength in aqueous media; (3) the flour paste requires a preservative system because it is an aqueous system, however, such preservatives can cause allergies; and (4) it is not possible to control the proportion of cleansing, exfoliating and moisturizing actions with such a method.

Thus, there is a need for stable personal care formulations containing no soap or a synthetic surfactant, providing simultaneous exfoliant, cleansing and moisturizing actions, requiring no preservative system, lending themselves to balancing the proportion of cleansing, exfoliant and moisturizing actions and not being irritating to the eyes.

SUMMARY

A general objective of the invention is to provide a non-aqueous personal care formulation which simultaneously has cleansing, exfoliant and moisturizing properties when applied to a user's skin. Further objectives of the invention include providing personal care formulations which: (1) are stable; (2) do not cause skin or eye irritation; (3) provide simultaneous exfoliation, cleansing and moisturization of the skin and hair without the use of soap or a synthetic surfactant; (4) do not require a preservative system; (5) have flexibility for adjustment of the proportion of cleansing, moisturizing and exfoliating effects; and (6) are convenient for routine use.

The general objective of the invention can be obtained, at least in part, via a non-aqueous personal care formulation containing or consisting of a high protein grain and/or legume flour dispersed in an oil phase. In accordance with certain embodiments, the personal care formulation can include or consist of a high protein grain and/or legume flour dispersed in an oil phase, preservatives, viscosity building agents, aesthetic enhancers and/or other functional ingredients such as Vitamin E, Aloe, Amla, herbs, and/or other medicinal ingredients.

Other objects and advantages will be apparent to those skilled in the art from the following detailed description taken in conjunction with the examples.

As used herein, the term "flour" refers to a finely divided particulate or powder product. The term flour further encompasses "meal" products which includes or contains the entire seed contents including the seed coat As used herein, the term "high protein flour" refers to flour products having a protein content of greater than 15 grams protein per 100 grams flour product, and, more particularly, flour products having a protein content of at least about 20 grams protein per 100 grams flour product. High protein flours include, for example, soy flour which typically has a protein content ranging from about 40 to about 55 grams per 100 grams flour, urad flour (black gram flour) and besan flour (chickpea flour) each of which contain at least 20 grams protein per 100 grams flour, and mung bean flour, which has protein content ranging from about 23 to about 54 grams protein per 100 grams flour. Other suitable high protein flours include, for example, black-eye bean or cowpea flour, green pea flour, and kidney bean flours which have reported protein contents of between about 18 to about 30 grams of protein per 100 grams of flour. In contrast, traditional wheat, oat and rice flours typically have a protein content ranging from about 6 to about 15 grams protein per 100 grams flour.

DETAILED DESCRIPTION

Figure 1:
FIGS. 1-6 disclose a method of using a skin care formulation having simultaneous cleansing, exfoliating and moisturizing properties.
Figure 2:
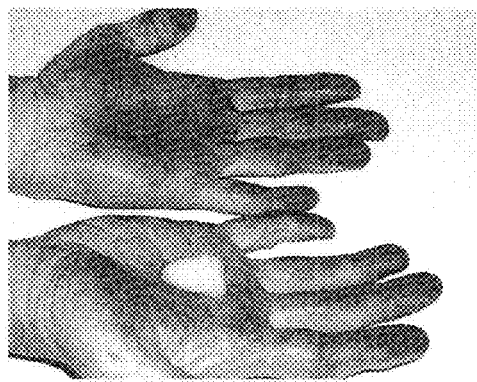
Figure 3:
Figure 4:
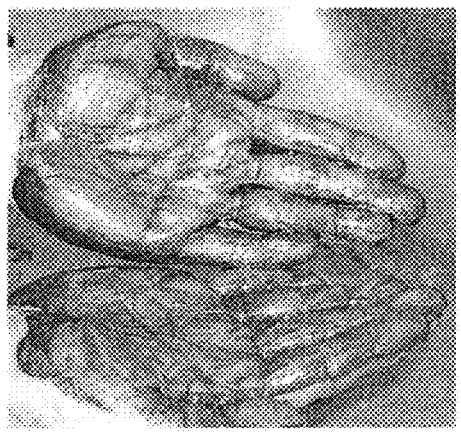

The invention provides a combination cleansing, exfoliating and moisturizing personal care formulation which is non-aqueous and can be used on the skin and/or hair. The formulation includes a particulate phase including or consisting of high protein grain and/or legume flour which is dispersed in an oil phase. The high protein grain and/or legume flour generally retains its crystalline structure and particle size in the oil and allowing the flour particles to act as both a natural emulsifier or surfactant and an exfoliant.

The oil phase can include or consist of mineral oil, petrolatum, a vegetable oil and/or a hydrogenated or partially hydrogenated vegetable oil. Suitable vegetable oils for use in the personal care formulation include sesame, coconut, almond, jojoba, corn, olive, palm kernel oil and combinations thereof.

The oil phase can also contain or consist of an oil combined with natural thickening agents and/or synthetic thickeners. Examples of suitable natural thickening agents include or consist of vegetable butters such as, for example, cocoa butter, shea butter, almond butter, soy butter, mango butter, pistachio butter, sal butter, macadamia nut butter, avocado butter, and combinations thereof. Suitable synthetic thickeners can include or consist of, for example, polyethylene glycols, gums, alginates, cellulose derivatives, and combinations thereof. Such natural thickening agents and/or synthetic thickeners can be added to the oil phase to provide physical stability to the personal care formulation to reduce or prevent separation and/or settling of the flour particles from the oil phase.

The particulate phase is a grain and/or legume flour phase which can include or consist of a high protein flour obtained from the grains or legumes of the species *Vigna radiata* (Green gram or mung beans), *Vigna mungo* (Black gram), *Glycine max* (Soy bean), *Cicer aerientinum* (Chick pea), *Vigna unguicalata* (black-eye beans, black-eye peas or cowpeas), *Pisum sativum* (green pea), *Phaseolus vulgaris* (kidney or pinto beans), and combinations thereof. Other high protein grains having emulsifying properties can alternatively and/or additionally be included in the particulate phase.

Advantageously, the personal care formulations of the present invention include a particulate or flour phase which includes or consists of a high protein flour because it has been surprisingly been discovered that grains and/or grain flours that are free of and/or have lower levels of plant proteins do not provide sufficient cleansing action when dispersed in a non-aqueous phase. For example, it has been surprisingly discovered that neither colloidal oatmeal powder nor oat flour when used in the formulations of the present invention exhibited cleansing action. Similarly, rice flour also lacked cleansing properties. It is believed that the lower levels of plant proteins typically or generally found in the oat, rice and/or wheat flours commonly utilized in commercial personal care formulations reduce ability of the flour to emulsify the oil phase which results in a reduced cleansing action when rubbed on skin and/or hair.

It is further believed that dispersing the high protein grain and/or legume flour in a non-aqueous oil phase improves both the exfoliating properties of the flour particles. It is theorized that dispersing the flour particles in a non-aqueous oil phase allows the particles to retain sufficient crystalline structure and particle size and therefore act as an effective exfoliant. In contrast, dispersion of flour in water or water-containing systems can reduce particle size and integrity as the grain flour and/or components of the grain flour dissolve in the aqueous fluid making it difficult to control its exfoliant properties.

The ratio of the oil phase to the grain flour may be adjusted in order to achieve a proper proportion of moisturizing effect to cleansing effect. Generally, the higher the ratio of the oil phase to the grain flour phase the higher the moisturizing effect because more of the oil phase is going to be left behind on the skin after cleansing.

In accordance with certain embodiments, the formulation can include or consist of about 20% to about 80% by weight of the oil phase and about 20% to about 80% by weight of the natural grain and/or legume derived surfactant phase. Alternatively, the formulations can include or consist of about 30% to about 75% by weight of the oil phase and about 25% to about 75% by weight of the natural grain and/or legume derived surfactant phase. The natural grain and/or legume derived surfactant phase can be in the form of a particulate flour product made from high protein grains and/or legumes. The formulations can further include or consist of about 0.5% to about 5% by weight additional components such as, for example, viscosity building agents, aesthetic enhancers, functional ingredients, and/or lathering agents.

The particle size of the grain flour may be adjusted to control the exfoliating properties of the non-aqueous formulations. Generally, the larger the particles size the better the exfoliating capacity.

In accordance with the invention, the formulations are totally non-aqueous and typically do not require preservatives. However, in accordance with certain embodiments, the personal care formulations can include or consist of a high protein grain and/or legume flour, an oil phase and one or more preservatives. Such preservatives may be added such as, for example, to stabilize the formulations for long term storage and/or shipment in harsher conditions.

In accordance with certain other embodiments, the personal care formulations can include or consist of a high protein grain and/or legume flour dispersed in an oil phase and in combination with additional viscosity building agents and/or aesthetic enhancers. Examples of suitable aesthetic enhancers include, for example, colors, fragrances and combinations thereof.

The personal care formulations can also, in some embodiments, include certain other functional ingredients to enhance the product. For example, the present invention comprehends personal care formulations which include or consist of a high protein grain and/or legume flour dispersed in an a oil phase in combination with one or more functional ingredients such as, for example, antioxidants like Vitamin E; Aloe, Amla (*Emblica officinalis*), herbs, medical ingredients and combinations thereof.

A non-aqueous personal care formulation in accordance with the invention can also include or consist of a high protein grain and/or legume flour dispersed in an oil phase in combination with a lathering agent. Such lathering agent can, for example, include or consist of a natural or plant derived material. One suitable natural or plant derived lathering agent which can be used in the non-aqueous personal care formulation includes or consists of Lauroyl Sarcosinate such as, for example, a Sodium Lauroyl Sarcosinate which is commercially available under the trade name Crodasinic LS-95.

Figure 5:
Figure 6:
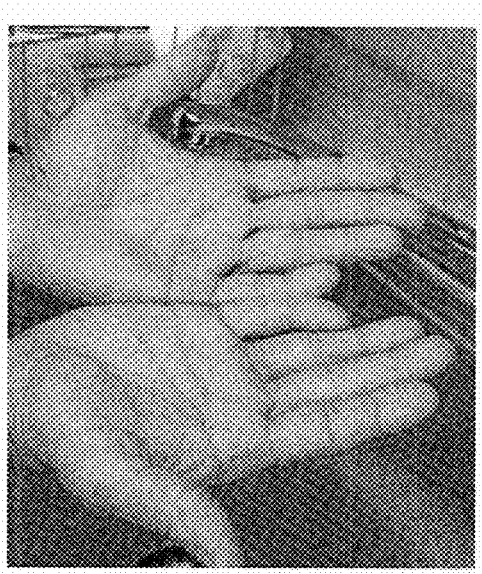

In practice, formulations prepared in accordance with invention can be used as a skin care formulation having simultaneous exfoliating, cleansing and moisturizing properties, a hand cleanser and moisturizer, a hair cleanser, and/or as a general cleanser. Referring to FIGS. 1-6, a method of using the formulations disclosed herein includes the steps of dispensing the formulation onto skin, hands, hair or other surface (FIG. 2), rubbing the formulation into or onto the surface without water to loosen or emulsify surface dirt, grease and/or oils (i.e., soilants) (FIG. 3), wetting the surface with a small amount of water, rubbing the water onto the surface to further emulsify the formulation and surface soilants (FIG. 4), and rinsing the surface with sufficient water to remove the emulsified formulation and surface soilants (FIGS. 5 and 6). The method can further or alternatively include the step of wetting the skin, hands, hair or other surface prior to dispensing the formulation onto the surface.

As can be seen in FIGS. 1-6, the formulations of the present invention such as, for example, the formulation presented in Table 21, below, are effective for removing grease and dirt obtained from the rim of a tire (FIG. 1) from the hands.

The invention may be further understood in connection with the following Examples.

EXAMPLES

Skin Care Formulations:

Example 1

Skin Exfoliant, Cleanser and Moisturizer

The non-aqueous personal care formulation of Example 1 includes the ingredients listed in Table 1 and prepared in accordance with procedure set forth in Table 2, below.

TABLE 1

| Ingredient | Amount per Batch (g) |
|---|---|
| White Petrolatum USP, Ultrapure SC | 215.0 |
| Light Mineral Oil, Food Grade | 125.0 |
| *Vigna radiata* Flour, passed through 80 mesh screen | 275.0 |
| Cocoa Butter, Deodorized | 100.0 |
| Jaffa Orange Fragrance, 106Y99 S/O #74720 | 5.0 |
| Total | 720.0 |

TABLE 2

| Step | Instructions |
|---|---|
| 1 | Heat white petrolatum and mineral oil in a stainless steel container at 50° ± 2° C. in an ultrasonic water bath while mixing with a homogenizing mixer. |
| 2 | Add *Vigna radiata* flour slowly while continuing mixing and mix for 10 minutes. |
| 3 | Add cocoa butter and continue mixing for 10 minutes. |
| 4 | Add fragrance and mix for another 5 minutes |
| 5 | Remove the container from the ultrasonic bath, place in a cold water bath and, while mixing with a spoon or spatula, let the formulation cool down to about 25° C.. |

Example 2

Skin Exfoliant, Cleanser and Moisturizer with a Lathering Agent

The non-aqueous personal care formulation of Example 2 consists of the ingredients listed in Table 3 and prepared in accordance with procedure set forth in Table 4, below.

TABLE 3

| Ingredient | Amount per Batch (g) |
|---|---|
| White Petrolatum USP, Ultrapure SC | 215.0 |
| Light Mineral Oil, Food Grade | 125.0 |
| *Vigna radiata* Flour, passed through 80 mesh screen | 275.0 |

TABLE 3-continued

| Ingredient | Amount per Batch (g) |
|---|---|
| Cocoa Butter, Deodorized | 100.0 |
| Crodasinic LS-95 | 15.0 |
| Jaffa Orange Fragrance, 106Y99 S/O #74720 | 5.0 |
| Total | 735.0 |

TABLE 4

| Step | Instructions |
|---|---|
| 1 | Heat white petrolatum and mineral oil in a stainless steel container at 50° ± 2° C. in an ultrasonic water bath while mixing with a homogenizing mixer. |
| 2 | Add *Vigna radiata* flour slowly while continuing mixing and mix for 10 minutes. |
| 3 | Add cocoa butter and continue mixing for 10 minutes. |
| 4 | Add Crodasinic LS-95 and mix for 10 minutes. |
| 5 | Add fragrance and mix for another 5 minutes |
| 6 | Remove the container from the ultrasonic bath, place in a cold water bath and, while mixing with a spoon or spatula, let the formulation cool down to about 25° C.. |

Example 3

Skin Exfoliant, Cleanser and Moisturizer with Less Exfoliant Action

The non-aqueous personal care formulation of Example 3 includes the ingredients listed in Table 5, below and prepared in accordance with procedure set forth in Table 2, above.

TABLE 5

| Ingredient | Amount per Batch (g) |
|---|---|
| White Petrolatum USP, Ultrapure SC | 215.0 |
| Light Mineral Oil, Food Grade | 125.0 |
| *Vigna radiata* Flour, passed through 120 mesh screen | 275.0 |
| Cocoa Butter, Deodorized | 100.0 |
| Jaffa Orange Fragrance, 106Y99 S/O #74720 | 5.0 |
| Total | 720.0 |

Example 4

Skin Exfoliant, Cleanser and Moisturizer with More Cleansing than Moisturizing Action The non-aqueous personal care formulation of Example 4 includes the ingredients listed in Table 6 and prepared in accordance with procedure set forth in Table 7, below.

TABLE 6

| Ingredient | Amount per Batch (g) |
|---|---|
| White Petrolatum USP, Ultrapure SC | 190.0 |
| Light Mineral Oil, Food Grade | 125.0 |
| *Vigna radiata* Flour, passed through 80 mesh screen | 300.0 |
| Cocoa Butter, Deodorized | 100.0 |
| Total | 715.0 |

TABLE 7

| Step | Instructions |
|---|---|
| 1 | Heat white petrolatum and mineral oil in a stainless steel container at 50° ± 2° C. in an ultrasonic water bath while mixing with a homogenizing mixer. |
| 2 | Add the flour slowly while continuing mixing. |
| 3 | Add cocoa butter and continue mixing until the cocoa butter is melted and mixed well. |
| 4 | Stop mixing and let the preparation cool down and fill into dispenser. |

Example 5

Skin Exfoliant, Cleanser and Moisturizer with More Cleansing than Moisturizing Action The non-aqueous personal care formulation of Example 5 includes the ingredients listed in Table 8, below, and prepared in accordance with procedure set forth in Table 7, above.

TABLE 8

| Ingredient | Amount per Batch (g) |
|---|---|
| White Petrolatum USP, Ultrapure SC | 190.0 |
| Light Mineral Oil, Food Grade | 125.0 |
| *Vigna mungo* Flour, passed through 80 mesh screen | 300.0 |
| Cocoa Butter, Deodorized | 100.0 |
| Total | 715.0 |

Example 6

Skin Exfoliant, Cleanser and Moisturizer with More Moisturizing than Cleansing Action The non-aqueous personal care formulation of Example 6 includes the ingredients listed in Table 9, below, and prepared in accordance with procedure set forth in Table 7, above.

TABLE 9

| Ingredient | Amount per Batch (g) |
|---|---|
| White Petrolatum USP, Ultrapure SC | 265.0 |
| Light Mineral Oil, Food Grade | 150.0 |
| *Vigna mungo* Flour, passed through 80 mesh screen | 200.0 |
| Cocoa Butter, Deodorized | 100.0 |
| Total | 715.0 |

Example 7

Skin Exfoliant, Cleanser and Moisturizer with More Cleansing than Moisturizing Action The non-aqueous personal care formulation of Example 7 includes the ingredients listed in Table 10, below, and prepared in accordance with procedure set forth in Table 7, above.

TABLE 10

| Ingredient | Amount per Batch (g) |
|---|---|
| White Petrolatum USP, Ultrapure SC | 190.0 |
| Light Mineral Oil, Food Grade | 125.0 |
| *Glycine max* Flour, passed through 80 mesh screen | 300.0 |
| Cocoa Butter, Deodorized | 100.0 |
| Total | 715.0 |

Example 8

Skin Exfoliant, Cleanser and Moisturizer with More Moisturizing than Cleansing Action The non-aqueous personal care formulation of Example 8 includes the ingredients listed in Table 11, below, and prepared in accordance with procedure set forth in Table 7, above.

TABLE 11

| Ingredient | Amount per Batch (g) |
|---|---|
| White Petrolatum USP, Ultrapure SC | 265.0 |
| Light Mineral Oil, Food Grade | 150.0 |
| *Cicer aerientinum* Flour, passed through 80 mesh screen | 200.0 |
| Cocoa Butter, Deodorized | 100.0 |
| Total | 715.0 |

Hair Care Products

Example 9

Shampoo

The non-aqueous personal care formulation of Example 9 includes the ingredients listed in Table 12 and prepared in accordance with procedure set forth in Table 13, below.

TABLE 12

| Ingredient | Amount per Batch (g) |
|---|---|
| Partially hydrogenated Palm Oil | 80.0 |
| Almond Oil | 50.0 |
| *Vigna radiata* Flour, passed through 120 mesh screen | 100.0 |
| Sodium Lauroyl Sarcosinate | 5.0 |
| Lemon Fragrance | 2.0 |
| Total | 237.0 |

TABLE 13

| Step | Instructions |
|---|---|
| 1 | Heat partially hydrogenated palm oil in a stainless steel container at 50° ± 2° C. in an ultrasonic water bath while mixing with a homogenizing mixer. |
| 2 | Add *Vigna radiata* flour slowly while continuing mixing and mix for 10 minutes. |
| 3 | Add almond oil and continue mixing for 10 minutes. |
| 4 | Add the sodium lauroyl sarcosinate and mix for 10 minutes. |
| 5 | Add fragrance and mix for another 5 minutes |
| 6 | Remove the container from the ultrasonic bath, place in a cold water bath and, While mixing with a spoon or spatula, let the formulation cool down to about 25° C.. |

Solid Personal Care Product.

Example 10

Exfoliating, Cleansing and Moisturizing Bar

The non-aqueous personal care formulation of Example 10 includes the ingredients listed in Table 14 and prepared in accordance with procedure set forth in Table 15, below.

TABLE 14

| Ingredient | Amount per Batch (g) |
| --- | --- |
| Partially hydrogenated Palm Oil | 100.0 |
| *Vigna radiata* Flour, passed through 80 mesh screen | 200.0 |
| Sodium Lauroyl Sarcosinate | 5.0 |
| *Aloe* Fragrance | 5.0 |
| Total | 310.0 |

TABLE 15

| Step | Instructions |
| --- | --- |
| 1 | Heat partially hydrogenated palm oil in a stainless steel container at 50° ± 2° C. in an ultrasonic water bath while mixing with a homogenizing mixer. |
| 2 | Add *Vigna radiata* flour slowly while continuing mixing and mix for 30 minutes. |
| 3 | Add the sodium lauroyl sarcosinate and mix for 10 minutes. |
| 4 | Add fragrance and mix for another 5 minutes. |
| 5 | Remove the container from the ultrasonic bath, place in a cold water bath and, while mixing with a spoon or spatula, let the formulation cool down to about 25° C.. |
| 6 | Fill into a soap mold and let cool. |

Shea Butter Formulations.

Example 11

Skin Exfoliant, Cleanser and Moisturizer with Olive Oil

The non-aqueous personal care formulation of Example 11 includes the ingredients listed in Table 16 and was prepared in accordance with procedure set forth in Table 17, below.

TABLE 16

| Ingredient | Amount per Batch (g) |
| --- | --- |
| Olive Oil | 150.0 |
| Shea Butter | 100.0 |
| *Vigna radiata* Flour, passed through 120 mesh screen | 275.0 |
| Total | 525.0 |

TABLE 17

| Step | Instructions |
| --- | --- |
| 1 | Heat oil in a stainless steel container at 50° ± 2° C. in an ultrasonic water bath while mixing with a homogenizing mixer. |
| 2 | Add the *Vigna radiata* flour slowly while continuing mixing. |
| 3 | Add shea butter and continue mixing until the shea butter is melted and mixed well. |
| 4 | Stop mixing and let the preparation cool to room temperature and fill into dispenser. |

Example 12

Skin Exfoliant, Cleanser and Moisturizer with Almond Oil

The non-aqueous personal care formulation of Example 12 includes the ingredients listed in Table 18, below, and was prepared in accordance with procedure set forth in Table 17, below.

TABLE 18

| Ingredient | Amount per Batch (g) |
| --- | --- |
| Almond Oil | 164.0 |
| Shea Butter | 100.0 |
| *Vigna radiata* Flour, passed through 120 mesh screen | 275.0 |
| Total | 539.0 |

Example 13

Skin Exfoliant, Cleanser and Moisturizer with Coconut Oil

The non-aqueous personal care formulation of Example 13 includes the ingredients listed in Table 19, below, and was prepared in accordance with procedure set forth in Table 17, above.

TABLE 19

| Ingredient | Amount per Batch (g) |
| --- | --- |
| Coconut Oil | 175.0 |
| Shea Butter | 100.0 |
| *Vigna radiata* Flour, passed through 120 mesh screen | 275.0 |
| Total | 550.0 |

Example 14

Skin Exfoliant, Cleanser and Moisturizer with Soy Bean Oil

The non-aqueous personal care formulation of Example 14 includes the ingredients listed in Table 20, below, and was prepared in accordance with procedure set forth in Table 17, above

TABLE 20

| Ingredient | Amount per Batch (g) |
| --- | --- |
| Soy Bean Oil | 600.0 |
| Shea Butter | 255.0 |
| *Vigna radiata* Flour, passed through 120 mesh screen | 915.0 |
| Total | 1770.0 |

Experimental Results

Ten (10) human participants were provided with a skin care formulation described in Table 21, below. The study partici pants used the formulation in the shower in place of soap for a period of fifteen (15) days. Participants were instructed to use the skin care formulation in the same manner as a soap or shower gel followed by towel drying of the skin. The use of moisturizers for the duration of the study was prohibited.

TABLE 21

| Ingredient | Amount per Batch (g) |
| --- | --- |
| White Petrolatum USP, Ultrapure SC | 2,150.0 |
| Light Mineral Oil, Food Grade | 1,250.0 |
| *Vigna radiata* Flour, passed through 120 mesh screen | 2,750.0 |
| Cocoa Butter, Deodorized | 1,000.0 |
| Fresh & Clean Fragrance | 25.0 |
| Total | 7,175.0 |

At the completion of the study period, the participants were asked to complete the questionnaire shown in Table 22, below.

TABLE 22

| | Test Parameter | Score |
| --- | --- | --- |
| 1 | Skin Dryness - Did the product help reduce skin dryness? | |
| 2 | Skin Itching - Did the product help reduce skin itching? | |
| 3 | Cleansing - Are you satisfied with the cleansing ability of this product? | |
| 4 | Moisturization - Are you satisfied with the moisturizing ability of this product? | |
| 5 | Exfoliation power - Are you satisfied with the exfoliation property of this product? | |
| 6 | Lathering - Are you satisfied with lathering of this product? | |
| 7 | Product consistency - Squeezability from the bottle, feel, etc. | |
| 8 | Product color - Are you satisfied with the color of this product? | |
| 9 | Fragrance - Are you satisfied with the fragrance of this product? | |
| 10 | Skin smoothness - Does you skin feel smooth? | |
| 11 | Eye Irritation - Did you feel any eye irritation when using this product? | |
| 12 | Would you use this product as a substitute for soap, if available commercially? | |
| 13 | Any adverse reactions: | |
| 14 | Comments & Suggestions: | |

Participants were asked to rank each of items 1-12 on scale of 0 to 10 with 0 being the lowest score and 10 being the highest score. Table 23, below, shows the average ranking for each items 1-12.

TABLE 23

| | Test Parameter | Average Score |
| --- | --- | --- |
| 1 | Skin Dryness - Did the product help reduce skin dryness? | 9.3 |
| 2 | Skin Itching - Did the product help reduce skin itching? | 8.8 |
| 3 | Cleansing - Are you satisfied with the cleansing ability of this product? | 8.3 |
| 4 | Moisturization - Are you satisfied with the moisturizing ability of this product? | 9.2 |
| 5 | Exfoliation power - Are you satisfied with the exfoliation property of this product? | 7.3 |
| 6 | Lathering - Are you satisfied with lathering of this product? | 6.8 |
| 7 | Product consistency - Squeezability from the bottle, feel, etc. | 7.0 |
| 8 | Product color - Are you satisfied with the color of this product? | 7.0 |
| 9 | Fragrance - Are you satisfied with the fragrance of this product? | 6.0 |
| 10 | Skin smoothness - Does you skin feel smooth? | 9.3 |
| 11 | Eye Irritation - Did you feel any eye irritation when using this product? | 0 |
| 12 | Would you use this product as a substitute for soap, if available commercially? | 9.1 |

The experimental data presented in Table 23 demonstrates that the formulation was effective as a cleanser, exfoliant and moisturizer. Further, the formulation had generally acceptable lathering, consistency, color and fragrance properties. Additionally, no adverse reactions or eye irritation was reported by the study participants.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

I claim:

1. A non-aqueous cleansing formulation, comprising:
   an oil phase; and
   a flour phase derived from a legume selected from the group consisting of *Vigna radiata, Vigna mungo, Cicer aerientinum, Vigna unguicalata, Pisum sativum, Phaseolus vulgaris*, and combinations thereof,
   wherein the flour phase is present in an amount from about 20% to about 80% by weight based on a total weight of the non-aqueous cleansing formulation.

2. The non-aqueous cleansing formulation according to claim 1, wherein the oil phase is petrolatum, mineral oil, a vegetable oil, a partially hydrogenated vegetable oil, a vegetable butter, or a combination thereof, and wherein the oil phase comprises from about 20% to about 80% by weight of the total weight of the non-aqueous cleansing formulation.

3. The non-aqueous cleansing formulation according to claim 2, wherein the vegetable oil is selected from the group consisting of coconut oil, sesame oil, almond oil, soy bean oil, olive oil, partially hydrogenated palm oil, and combinations thereof.

4. The non-aqueous cleansing formulation according to claim 2, wherein the vegetable butter is selected from the group consisting of cocoa butter, shea butter, almond butter, soy butter, mango butter, pistachio butter, sal butter, macadamia nut butter, avocado butter, and combinations thereof.

5. The non-aqueous cleansing formulation according to Claim 1, wherein the flour phase is a particulate material.

6. The non-aqueous cleansing formulation according to claim 1, further comprising an additive selected from the group consisting of preservatives, fragrances, colorants, and combinations thereof.

7. The non-aqueous cleansing formulation according to claim 1, wherein the formulation is free of materials selected from the group consisting of synthetic soaps, synthetic surfactants, and combinations thereof.

8. The non-aqueous cleansing formulation according to claim 1, further comprising a lathering agent.

9. The non-aqueous cleansing formulation according to claim 1, wherein the formulation is effective as a cleanser, a moisturizer and an exfoliant.

10. The non-aqueous cleansing formulation according to claim 1, wherein the formulation is effective as a skin care formulation having cleansing, moisturizing, and exfoliant properties, a hand cleanser having cleansing and moisturizing properties, a hair cleanser, a general cleanser, or combinations thereof.

11. The non-aqueous cleansing formulation of claim 1, wherein the flour phase is present in an amount from about 51% to about 80% by weight based on total weight of the non-aqueous cleansing formulation.

12. A method for use of the non-aqueous cleansing formulation according to claim 1, comprising:
rubbing the formulation onto a wet or dry surface of a body, hands, hair or face;
wetting the surface with water;
rubbing the water onto the surface to emulsify the formulation and any surface soilants; and
rinsing the surface with sufficient water to remove the emulsified formulation and said surface soilants.

13. A non-aqueous cleansing formulation comprising:
an oil phase including an oil component and a thickening agent; and
a natural surfactant comprising a flour selected from the group consisting of *Vigna radiata, Vigna mungo, Cicer aerientinum, Vigna unguicalata, Pisum sativum, Phaseolus vulgaris*, and combinations thereof,
wherein the cleansing formulation is free of synthetic soaps and synthetic surfactants, and
wherein the formulation comprises from about 25% to about 75% by weight natural surfactant based on a total weight of the non-aqueous cleansing formulation.

14. The non-aqueous cleansing formulation according to claim 13, wherein the oil component is selected from the group consisting of petrolatum, mineral oil, a vegetable oil, a partially hydrogenated vegetable oil, and combinations thereof.

15. The non-aqueous cleansing formulation according to claim 13, wherein the thickening agent comprises a vegetable butter selected from the group consisting of cocoa butter, shea butter, almond butter, soy butter, mango butter, pistachio butter, sal butter, macadamia nut butter, avocado butter, and combinations thereof.

16. The non-aqueous cleansing formulation according to claim 13, wherein the flour has a protein content of greater than about 15 grams protein per 100 grams flour.

17. A non-aqueous cleansing formulation comprising:
an oil component;
a thickening agent selected from the group consisting of cocoa butter, shea butter, almond butter, soy butter, mango butter, pistachio butter, sal butter, macadamia nut butter, avocado butter, and combinations thereof; and
a natural surfactant comprising a flour selected from the group consisting of *Vigna radiata, Vigna mungo, Cicer aerientinum, Vigna unguicalata, Pisum sativum, Phaseolus vulgaris*, and combinations thereof,
wherein the flour product has a protein content of at least about 20 grams protein per 100 grams of flour.

18. The non-aqueous cleansing formulation according to claim 17, wherein the natural surfactant is present in an amount from about 20% to about 80% by weight or from about 25% to about 75% by weight based on a total weight of the non-aqueous cleansing formulation.

19. The non-aqueous cleansing formulation according to claim 17, wherein the cleansing formulation is free of synthetic soaps and synthetic surfactants.

* * * * *